United States Patent
Yoshida et al.

(10) Patent No.: US 7,166,136 B2
(45) Date of Patent: Jan. 23, 2007

(54) HAIRDYE PREPARATION

(75) Inventors: Katsunori Yoshida, Yokohama (JP); Haruhiko Inoue, Yokohama (JP); Koichi Kinoshita, Yokohama (JP); Masatoshi Ochiai, Yokohama (JP); Katsuo Hashimoto, Yokohama (JP); Yasunari Nakama, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 350 days.

(21) Appl. No.: 10/502,356

(22) PCT Filed: Jan. 28, 2002

(86) PCT No.: PCT/JP02/00586

§ 371 (c)(1), (2), (4) Date: Jul. 23, 2004

(87) PCT Pub. No.: WO03/063812

PCT Pub. Date: Aug. 7, 2003

(65) Prior Publication Data

US 2005/0071931 A1   Apr. 7, 2005

(51) Int. Cl.
*A61K 7/13* (2006.01)
(52) U.S. Cl. .................. 8/405; 8/455; 8/463; 8/581; 8/587; 8/588; 8/594; 8/611; 8/658
(58) Field of Classification Search .............. 8/405, 8/455, 463, 581, 587, 588, 594, 611, 658
See application file for complete search history.

(56) References Cited

U.S. PATENT DOCUMENTS 5,332,581 A * 7/1994 Yoshihara et al. ......... 424/70.1

FOREIGN PATENT DOCUMENTS

| JP | 61-022007 | 1/1986 |
| JP | 5-051309 | 3/1993 |
| JP | 8-183716 | 7/1996 |
| JP | 2001-089335 | 4/2001 |
| JP | 2001-213737 | 8/2001 |
| JP | 2001-213738 | 8/2001 |
| JP | 2001-213739 | 8/2001 |
| JP | 2002-003344 | 1/2002 |
| KR | 123072 | 11/1997 |

OTHER PUBLICATIONS

STIC Search Report (Aug. 14, 2006).*

* cited by examiner

*Primary Examiner*—Eisa Elhilo
(74) *Attorney, Agent, or Firm*—Snider & Associates; Ronald R. Snider

(57) ABSTRACT

A hair dye composition comprising a component (A), which is a specified long-chain acyl sulfonic acid salt anionic surfactant, in an amount of 0.1 to 10.0 wt. %; a component (B), which is an aliphatic alcohol, in an amount of 0.25 to 25.0 wt. %; and a component (C), which is an acid dye and/or a natural dyestuff. The hair dye composition is stable even in a strongly acidic region (pH 1.5 to 4.5) where it exerts a dyeing effect. It has an appropriate viscosity and provides excellent sensation upon use. Furthermore, the composition can be easily rinsed off after use thereof.

4 Claims, No Drawings

HAIRDYE PREPARATION

TECHNICAL FIELD

The present invention relates to a hair dye composition. More particularly, the present invention relates to an acidic hair dye composition which exhibits excellent stability and dyeability, which provides excellent sensation upon use (smoothness), and which can be easily rinsed off after use thereof.

BACKGROUND ART

Hair dye compositions for dyeing the hair are widely employed as, for example, "dyes for concealing gray (or, white) hair" or "dyes for imparting fashionable color." Such a hair dye composition contains, as a matter of course, a coloring agent for dyeing the hair a desired color. Among such coloring agents, an "acid dye," which exerts its hair dyeing effects to the maximum extent in an acidic region, is considered to be one of the most desirable coloring agents, since an acid dye exhibits excellent safety. Particularly, an azo acid dye is typically employed as a coloring agent for "semi-permanent hair dye compositions," which are designed to impart semi-permanent dyeing effects to the hair. Therefore, there is a great need for an acid dye in hair dye compositions.

During use of an "acidic hair dye composition," which contains an acid dye as a coloring agent, the pH of the composition must be regulated to fall within a strongly acidic region (i.e., pH of 1.5 to 4.5). In some cases, an acidic hair dye composition contains, in addition to an acid dye, a natural dyestuff in view of, for example, dyeability and color tone. When a natural dyestuff is incorporated into an acidic hair dye composition, desirably, the composition is used in an acidic region, in order to reduce, for example, stimulation to the hair. Therefore, a natural dyestuff which can exerts its dyeing effects in such an acidic region is desirably employed. Meanwhile, in general, a thickner is incorporated into such a strongly acidic hair dye composition, in order to prevent the composition from running through the hair upon use and from coming into contact with an object other than the hair.

However, considerable limitations are imposed on the thickner which can be employed in such a strongly acidic pH region, and even the thickner that is considered to be usable in a strongly acidic region is not necessarily satisfactory as a thickner to be incorporated into a hair dye composition. Conventionally, xanthan gum has been generally employed as a thickner in acidic hair dye compositions (Japanese Patent Publication (kokoku) No. 2-32253). Meanwhile, there has been proposed a hair dye composition containing, in addition to xanthan gum, bentonite and/or cross-linked sodium polyacrylate, which serves as an improving agent (Japanese Patent Application Laid-Open (kokai) No. 5-51309.

However, although a conventionally known hair dye composition containing xanthan gum is stable at a pH of 4.5 or higher, the composition undergoes considerable change in viscosity in a strongly acidic region (i.e., pH of 1.5 to 4.5), in which the composition exerts its dyeing effects; i.e., the composition involves problems in terms of stability. In addition, the hair dye composition exhibits poor fluidity, and when the composition is applied to the hair with the hand, in some cases, the composition forms a lump and runs off through the hair, or the composition is difficult to spread on the hair. Furthermore, the hair dye composition provides a sticky sensation upon use; i.e., the composition does not provide satisfactory sensation upon use.

Therefore, as described above, a hair dye composition containing bentonite and/or cross-linked sodium polyacrylate in combination with xanthan gum has been proposed for improving the aforementioned fluidity. However, the hair dye composition still poses a problem in terms of stability, and also involves other problems; for example, the composition cannot be easily rinsed off after use thereof.

Conventionally, there has been incorporated, into a product which is applied to the hair and then rinsed off, a rinse gel which is prepared from a combination of a long-chain alkyl alcohol and a cationic surfactant such as an alkyltrimethylammonium salt, in order to impart smoothness to the hair and reduce unruly dryness of the hair. However, such a cationic rinse gel cannot be incorporated into an acidic hair dye composition, since, when the dye contained in the composition, which is anionic, coexists with a cationic component, an ionic complex is formed in the composition, leading to generation of insoluble precipitates in the composition. Therefore, a conventional acidic hair dye composition involves problems in terms of sensation upon use, including any tactile frictional resistance between hair fibers during rinsing, and unruliness of the hair after the hair is dried.

In view of the foregoing, an object of the present invention is to provide a hair dye composition which is stable even in a strongly acidic region (pH of 1.5 to 4.5) in which an acid dye exerts its dyeing effects, which exhibits appropriate viscosity, which provides excellent sensation upon use, and which can be easily rinsed off after use thereof.

DISCLOSURE OF THE INVENTION

In order to solve the aforementioned problems, the present invention provides a hair dye composition comprising a component (A); i.e., a long-chain acyl sulfonic acid salt anionic surfactant represented by the following formula (I):

$$R_1CO\text{-a-}(CH_2)_nSO_3M_1 \qquad (I),$$

wherein $R_1CO$— represents a saturated or unsaturated fatty acid residue (acyl group) having an average carbon atom number of 10 to 22; a represents —O— or —NR—, wherein R represents a hydrogen atom or a C1–C3 alkyl group; $M_1$ represents a hydrogen atom, an alkali metal, an alkaline earth metal, an ammonium, or an organic amine; and n represents an integer of 1 to 3, in an amount of 0.1 to 10.0 wt. %; a component (B); i.e., an aliphatic alcohol, in an amount of 0.25 to 25.0 wt. %; and a component (C); i.e., an acid dye and/or a natural dyestuff.

In the hair dye composition, the ratio by weight of the component (A) to the component (B) is preferably 1:2.5 to 1:50.

Preferred examples of the component (A) include a long-chain acyl isethionic acid salt anionic surfactant for the case where a of formula (I) is —O—, a long-chain acyl taurine salt anionic surfactant for the case where a of formula (I) is —NH—, and a long-chain acyl methyl taurine salt anionic surfactant for the case where a of formula (I) is —N(CH$_3$)—.

BEST MODE FOR CARRYING OUT THE INVENTION

The present invention will next be described in detail.

In the hair dye composition of the present invention, the component (A); i.e., the long-chain acyl sulfonic acid salt anionic surfactant, is represented by the following formula (I):

$$R_1CO\text{-}a\text{-}(CH_2)_nSO_3M_1 \quad (I)$$

In formula (I), $R_1CO$— represents a saturated or unsaturated fatty acid residue (acyl group) having an average carbon atom number of 10 to 22. Examples of $R_1CO$ include $C_{11}H_{23}CO$, $C_{12}H_{25}CO$, $C_{13}H_{27}CO$, $C_{14}H_{29}CO$, $C_{15}H_{31}CO$, $C_{16}H_{33}CO$, $C_{17}H_{35}CO$, a coconut fatty acid residue, and a palm fatty acid residue. $R_1CO$ is more preferably a fatty acid residue having an average carbon atom number of 12 to 22 in consideration of safety and other factors.

In formula (I), a represents —O— or —NR— (wherein R represents a hydrogen atom or a C1–C3 alkyl group), which is an electron donor group. Preferably, a is —O—, —NH—, or —N(CH$_3$)—.

In formula (I), $M_1$ represents a hydrogen atom, an alkali metal, an alkaline earth metal, an ammonium, or an organic amine. Examples of $M_1$ include lithium, potassium, sodium, calcium, magnesium, ammonium, monoethanolamine, diethanolamine, triethanolamine, sodium taurate, and sodium N—methyl taurate.

In formula (I), n represents an integer of 1 to 3, with 2 being preferred.

Examples of compounds for the case where a of formula (I) is —O—; i.e., long-chain acyl isethionic acid salt anionic surfactants, include cocoyl isethionic acid salts, stearoyl isethionic acid salts, lauroyl isethionic acid salts, and myristoyl isethionic acid salts.

Examples of compounds for the case where a of formula (I) is —NH—; i.e., long-chain acyl taurine salt anionic surfactants, include N-lauroyl taurine salts, N-cocoyl taurine salts, N-myristoyl taurine salts, and N-stearoyl taurine salts.

Examples of compounds for the case where a of formula (I) is —N(CH$_3$)—; i.e., long-chain acylmethyl taurine salt anionic surfactants, include N-lauroyl-N-methyl taurine salts, N-palmitoyl-N-methyl taurine salts, N-stearoyl-N-methyl taurine salts, and N-cocoyl-N-methyl taurine salts.

Of these, an N-stearoyl-N-methyl taurine salt is particularly preferred as the component (A). The component (A) may be one or more species selected from among long-chain acyl sulfonic acid salt anionic surfactants.

The amount of the component (A) is 0.1 to 10.0 wt. %, preferably 0.5 to 5.0 wt. %, on the basis of the entirety of the hair dye composition. When the amount of the component (A) is less than 0.1 wt. %, stability of the composition is lowered due to precipitation of crystals of the aliphatic alcohol (component (B)) and smoothness fails to be obtained during rinsing of the composition, whereas when the amount of the component (A) exceeds 10.0 wt. %, stability and safety of the composition are lowered because of reduction in viscosity.

The aliphatic alcohol serving as the component (B) is preferably a C12–C22 aliphatic alcohol having a straight or branched alkyl chain. Examples of the component (B) include straight-chain alcohols such as lauryl alcohol, cetyl alcohol, stearyl alcohol, behenyl alcohol, myristyl alcohol, oleyl alcohol, cetostearyl alcohol, hydrogenated rapeseed oil alcohol, and jojoba alcohol; and branched-chain alcohols such as monostearyl glyceryl ether (batyl alcohol), 2-decyltetradecinol, lanolin alcohol, cholesterol, phytosterol, hexyldodecanol, isostearyl alcohol, and octyldodecanol. In the present invention, straight-chain alcohols are preferably employed. The component (B) may be one or more species selected from among such aliphatic alcohols.

The amount of the component (B) is 0.25 to 25.0 wt. % on the basis of the entirety of the hair dye composition. When the amount of the component (B) is less than 0.25 wt. %, stability of the composition is lowered due to reduction in viscosity, whereas when the component (B) exceeds 25.0 wt. %, smoothness fails to be obtained during rinsing of the composition, and the hair dyeing effect of the composition is lowered.

In the present invention, the components (A) and (B) together form a gel. Since the thus-formed gel exhibits very high stability as compared with a conventional cationic rinse gel formed of a trimethylammonium cationic surfactant and a long-chain alkyl alcohol (i.e., aliphatic alcohol), the amount of a hair dye aid (e.g., benzyl alcohol) to be incorporated into the composition can be increased. Therefore, a hair dye composition exhibiting higher dyeability than that of a conventional hair dye composition can be prepared.

Since the gel formed of the components (A) and (B) is anionic, the gel does not form a complex with the below-described component (C) (i.e., an acid dye or natural dyestuff), and thus can stably coexist with the component (C). Therefore, there can be prepared a hair dye composition which provides a smooth sensation upon use that has not yet been obtained from a conventional hair dye composition, and which exhibits excellent stability (in particular, viscosity stability) and excellent dyeability.

In the present invention, in order to effectively form the aforementioned gel, the ratio by weight of the component (A) to the component (B) is preferably regulated to 1:2.5 to 1:50.

No particular limitations are imposed on the acid dye serving as the component (C), so long as it can be employed in a hair dye composition. Examples of the acid dye include nitro dyes, azo dyes, nitroso dyes, triphenylmethane dyes, xanthene dyes, quinoline dyes, anthraquinone dyes, and indigo dyes. Specific examples include Red No. 2, Red No. 3, Red No. 102, Red No. 104, Red No. 105, Red No. 106, Red No. 201, Red No. 220, Red No. 227, Red No. 230, Red No. 231, Red No. 232, Red No. 401, Red No. 502, Red No. 503, Red No. 504, Red No. 506, Red No. 602, Yellow No. 4, Yellow No. 5, Yellow No. 6, Yellow No. 202, Yellow No. 203, Yellow No. 402, Yellow No. 403, Yellow No. 406, Yellow No. 407, Orange No. 203, Orange No. 205, Orange No. 207, Orange No. 402, Green No. 3, Green No. 201, Green No. 204, Green No. 205, Green No. 206, Green No. 401, Green No. 402, Blue No. 1, Blue No. 2, Blue No. 202, Blue No. 205, Violet No. 401, Brown No. 201, and Black No. 401.

Among acid dyes, examples of oil dyes include Red No. 215, Red No. 218, Red No. 225, Orange No. 201, Orange No. 206, Yellow No. 201, Yellow No. 204, Green No. 202, Violet No. 201, Red No. 501, Red No, 505, Orange No. 403, Yellow No. 404, Yellow No. 405, and Blue No. 403.

No particular limitations are imposed on the natural dyestuff, so long as it can be employed in a hair dye composition. Examples of the natural dyestuff include carotenoid dyes, anthraquinone dyes, flavonoid dyes (anthocyanin dyes, chalcone dyes, and flavone dyes), porphyrin dyes, diketone dyes, betacyanin dyes, and azaphilon dyes. Specific examples of the natural dyestuff include madder color, annatto extract, paprika color, gardenia yellow, carotene extract, cochineal extract, lac color, red cabbage color, perilla color, purple corn color, elderberry color, boysenberry color, grape skin color, grape juice color, purple sweet potato color, carthamus yellow, carthamus red, kaoliang color, onion color, cacao color, sandalwood color, spirulina blue, chlorophyll, turmeric oleoresin, beet red, monascus red, monascus yellow, gardenia blue, and gardenia red. When such a natural dyestuff is incorporated into the hair dye composition, it desired, the natural dyestuff may be used in combination with, for example, an organic acid or an inorganic acid, thereby adjusting the pH of the composition to an appropriate value.

The component (C) may be one or more species selected from among acid dyes and natural dyestuffs.

The amount of the component (C) is preferably 0.001 to 2.0 wt. % on the basis of the entirety of the hair dye composition. When the amount of the component (C) is less than 0.001 wt. %, the hair dyeing effect of the composition becomes insufficient, whereas when the amount of the component (C) exceeds 2.0 wt. %, the degree of staining of the hand with the composition is increased, and safety of the composition tends to be lowered.

The hair dye composition of the present invention contains the aforementioned components (A) to (C) as essential components. Therefore, the composition can maintain very stable viscosity even in a low pH range in which the component (C) exerts its effects; for example, in a pH range as low as about 1.5 to about 4.5, since the components (A) and (B) together form a gel. In addition, the composition ensures excellent handling in use, and exhibits excellent hair dyeability.

The hair dye composition of the present invention exhibits low rate of change in viscosity; i.e., the composition exhibits excellent viscosity stability. Specifically, when, for example, the hair dye composition of the present invention is stored at a temperature of 45° C. for 28 days, and then the rate of change in viscosity of the composition is obtained by the below-described formula for evaluating the long-term viscosity stability of the composition, the rate of change in viscosity is found to be 0.8 to 1; i.e., the composition exhibits excellent long-term viscosity stability.

Rate of change in viscosity=(viscosity after storage at 45° C. for 28 days)/(viscosity one hour after production)

The viscosity of the hair dye composition of the present invention can be measured by use of a B-viscometer. The composition preferably has a viscosity of about 2,000 to about 50,000 m·Pas (25° C.). However, the composition may have a viscosity in excess of 50,000 m·Pas.

If desired, the hair dye composition of the present invention may contain an optional component in addition to the aforementioned essential components.

Examples of such an optional component include organic acids, inorganic acids, and salts thereof, which serve as a pH adjusting agent for adjusting the pH of the hair dye composition of the present invention so as to fall within a strongly acidic region. Examples of organic acids and salts thereof include propanoic acid, butanoic acid, butanedioic acid, pentanoic acid, hexanedioic acid, citric acid, lactic acid, tartaric acid, phthalic acid, L-glutamic acid, glycolic acid, DL-glutamic acid, taurine, N-methyl taurine, trisodium citrate, and sodium lactate. Examples of inorganic acids and salts thereof include carbonic acid, hydrochloric acid, sulfuric acid, phosphoric acid, sodium chloride, and potassium chloride. Of these, lactic acid, citric acid, tartaric acid, glycolic acid, and salts thereof, which are generally employed in cosmetics, are preferably employed.

The hair dye composition may contain a conventionally employed hair dye aid, in order to further improve the dyeability of the acid dye or the natural dyestuff. Examples of such a hair dye aid include an aromatic alcohol represented by the following formula (II):

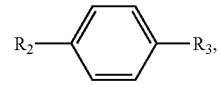

wherein $R_2$ represents a hydrogen atom, a methyl group, or a methoxy group; and $R_3$ represents —$CH_2OH$, —$CH_2CH_2OH$, —$CH(CH_3)OH$, —$CH_2CH_2CH_2OH$, —$C(CH_3)_2OH$, —$CH_2CH(CH_3)OH$, —$CH(CH_3)CH_2OH$, —$CH=CHCH_2OH$, or —$OCH_2CH_2OH$, a monohydric aliphatic alcohol, and a polyhydric aliphatic alcohol.

Specific examples of the aromatic alcohol include benzyl alcohol, phenethyl alcohol, γ-phenylpropyl alcohol, cinnamyl alcohol, anise alcohol, p-methylbenzyl alcohol, α-dimethylphenethyl alcohol, α-phenylethanol, and phenoxyethanol. Of these, benzyl alcohol is preferred, from the viewpoint of, for example, dyeing effects.

Specific examples of the monohydric aliphatic alcohol include ethanol, butanol, isopropanol, and cyclohexanol.

Specific examples of the polyhydric aliphatic alcohol include ethylene glycol, propylene glycol, butylene glycol, dipropylene glycol, hexylene glycol, isoprene glycol, and glycerin.

In addition to the aforementioned alcohols, for example, N-methylpyrrolidone, methyl cellosolve, ethyl cellosolve, methyl carbitol, or ethyl carbitol may be employed.

These hair dye aids may be incorporated singly or in combination of two or more species. The amount of the hair dye aid to be incorporated is preferably 0.5 to 15 wt. %, more preferably 1 to 10 wt. %, on the basis of the entirety of the hair dye composition.

The hair dye composition may contain a non-volatile-silicone-containing conditioning component, in order to further improve sensation upon use. Preferred examples of such a component include dimethylpolysiloxane, methylphenylpolysiloxane, amino-modified polysiloxane, and polyether silicone. Non-volatile silicone is generally incorporated into the hair dye composition in the form of oil solution, but may be incorporated in the form of emulsion.

In the case where non-volatile silicone is added in the form of emulsion, the emulsion may be prepared through mechanical dispersion or emulsion polymerization. No particular limitations are imposed on the particle size of the silicone to be employed, but the particle size is preferably about 10 nm to about 1 mm. The silicone may be in the form of oil, rubber, resin, or powder, and may assume a linear or cross-linked form. No particular limitations are imposed on the viscosity of the silicone.

If necessary, the hair dye composition of the present invention may contain, in addition to the aforementioned components, a component which is generally employed in hair dye compositions, so long as the component does not impede the effects of the present invention. Examples of such an additional component include a cationic surfactant, a lanolin derivative, a protein derivative, an oil component, a humectant component, a plant extract such as a crude drug, a cationic, anionic, or nonionic water-soluble polymer, a sequestering agent, a preservative, a bactericide, a UV absorbing agent, an antioxidant, a coloring agent, and a perfume.

The hair dye composition of the present invention preferably has a buffer capacity of 0.001 to 2.0 g-equivalent/L. As used herein, the term "buffer capacity" refers to a value determined by the following formula while using, as a scale, the concentration of a base required to raise the pH of a 10% aqueous solution of the hair dye composition at 25° C. by 1 from an initial pH value.

Buffer capacity=dCs/dpH, wherein Cs represents an ion concentration (g-equivalent/L) of the base.

The hair dye composition of the present invention is suitable for use as a one-part hair dye composition, and can be applied to, for example, hair manicure or color rinse.

EXAMPLES

The present invention will next be described in more detail by way of Examples, which should not be construed as limiting the invention thereto. The amount of each component of a sample is represented by "wt. %."

Examples 1 through 16 and Comparative Examples 1 through 10

Samples having the compositions shown in the below-described Tables 1 through 6 were prepared by means of a customary method. On the basis of the below-described evaluation criteria, each of the samples was evaluated in terms of the following: texture of hair after use of the sample (smoothness), texture of hair during rinsing of the sample (smoothness), stability (viscosity), stability (turbidity, precipitation, and separation), and degree of staining of the skin. The results are shown in Tables 1 through 6.

"Emulsion-polymerized dimethylpolysiloxane(*)" shown in Tables 1 through 6 has a silicone particle size of 200 nm, a viscosity of 100,000 cs (25° C.), and an active component content of 40 wt. %.

[Texture of Hair after use of the Sample (Smoothness)]

Hair fibers having a length of about 15 cm and a diameter of about 70 to about 90 μm, which is the average diameter of hair fibers among Japanese people, were formed into a tress (10 g), and the thus-formed hair tress was employed for evaluation.

Each of the samples (1 g) was manually applied to the hair tress, and then the sample was rinsed off while shaken for two minutes in a water bath containing 40° C. tap water (300 ml). Thereafter, the resultant hair tress was allowed to stand for 24 hours at a humidity of 50% and a temperature of 25° C. Subsequently, the resultant hair tress was touched by the hands of 20 panelists, and texture of the hair tress was evaluated on the basis of the following evaluation criteria.

(Evaluation Criteria)

AA: 16 or more of 20 panelists commented that the hair tress had improved smoothness, compared to the hair tress before staining.

BB: 12 to 15 of 20 panelists commented that the hair tress had improved smoothness, compared to the hair tress before staining.

CC: 8 to 11 of 20 panelists commented that the hair tress had improved smoothness, compared to the hair tress before staining.

DD: 7 or less of 20 panelists commented that the hair tress had improved smoothness, compared to the hair tress before staining.

[Texture of Hair during Rinsing of the Sample (Smoothness)]

Each of the samples was used in practice by 20 male expert panelists for sensory evaluation. After the hair of each panelist was washed with shampoo, the sample (about 3 g) was applied to the hair, and then allowed to stand for five minutes. Thereafter, the sample was rinsed off with water of about 40° C. Texture of the hair during rinsing of the sample was evaluated on the basis of the following evaluation criteria.

(Evaluation Criteria)

AA: 16 or more of 20 panelists commented that the hair exhibited smoothness during rinsing of the sample.

BB: 12 to 15 of 20 panelists commented that the hair exhibited smoothness during rinsing of the sample.

CC: 8 to 11 of 20 panelists commented that the hair exhibited smoothness during rinsing of the sample.

DD: 7 or less of 20 panelists commented that the hair exhibited smoothness during rinsing of the sample.

[Stability (Viscosity)]

One hour following production, each of the samples was subjected to measurement of viscosity at 30° C. by use of a B-viscometer (12 rpm/min).

Separately, following production, the sample was stored in a thermostatic chamber at 45° C. for 28 days, and subsequently stored in a thermostatic chamber at 30° C. for one hour. Thereafter, the viscosity of the sample was measured at 30° C. by use of a B-viscometer (12 rpm/min).

The rate of change in viscosity of the sample was calculated by use of the following formula, and the sample was evaluated on the basis of the below-described evaluation criteria.

Rate of change in viscosity=(viscosity after storage at 45° C. for 28 days)/(viscosity one hour after production)

(Evaluation Criteria)

BB: Rate of change in viscosity is 0.8 to 1.

CC: Rate of change in viscosity is 0.6 or more and less than 0.8.

DD: Rate of change in viscosity is less than 0.6.

[Stability (Turbidity, Precipitation, and Separation)]

Each of the above-produced samples was stored for 28 days in a thermostatic chamber whose temperature was maintained at 45° C., 25° C., or −5° C. Thereafter, the resultant sample was visually observed, and evaluated on the basis of the following evaluation criteria.

(Evaluation Criteria)

BB: Turbidity, precipitation, and separation did not occur in the sample at any of the above temperature levels.

CC: Turbidity, precipitation, and separation occurred in the sample at any one of the above temperature levels.

DD: Turbidity, precipitation, and separation occurred in the sample at two or more of the above temperature levels.

[Degree of Staining of the Skin]

Each of the samples was used in practice by 20 female expert panelists for sensory evaluation. After the hair of each panelist was washed with shampoo, the sample (about 3 g) was applied to the hair, and then allowed to stand for three minutes. Thereafter, the sample was rinsed off with water of about 40° C., and moisture was wiped off the hand with a towel. Subsequently, the degree of staining of the skin with the sample was evaluated on the basis of the following evaluation criteria.

(Evaluation Criteria)

AA: 16 or more of 20 panelists commented that the degree of staining of the skin falls within an acceptable range.

BB: 12 to 15 of 20 panelists commented that the degree of staining of the skin falls within an acceptable range.

CC: 8 to 11 of 20 panelists commented that the degree of staining of the skin falls within an acceptable range.

DD: 7 or less of 20 panelists commented that the degree of staining of the skin falls within an acceptable range.

TABLE 1

|  | Ex. 1 | Ex. 2 | Ex. 3 | Ex. 4 | EX. 5 |
|---|---|---|---|---|---|
| Sodium N-stearoyl-N-methyl taurate | 2.0 | — | — | 0.1 | 1.0 |
| Sodium cocoyl isethionate | — | 2.0 | — | — | — |
| Sodium N-palmitoyl taurate | — | — | 2.0 | — | — |
| Sodium stearyl sulfate | — | — | — | 2.0 | — |
| Stearyl alcohol | 8.0 | 8.0 | 8.0 | — | — |
| Behenyl alcohol | — | — | — | 2.5 | 5.0 |
| Dimethylpolysiloxane (6 cs) | 2.0 | 2.0 | 2.0 | — | 2.0 |
| Emulsion-polymerized dimethylpolysiloxane(*) | 2.0 | 2.0 | 2.0 | 2.0 | — |
| Black No. 401 | 0.2 | 0.2 | 0.2 | 0.2 | 0.2 |
| Violet No. 401 | 0.3 | 0.3 | 0.3 | 0.3 | 0.3 |
| Yellow No. 4 | 0.3 | 0.3 | 0.3 | 0.3 | 0.3 |
| Benzyl alcohol | 4.0 | 4.0 | 4.0 | 4.0 | 4.0 |
| Citric acid | Appropriate amount | Appropriate amount | Appropriate amount | Appropriate amount | Appropriate amount |
| Preservative | Appropriate amount | Appropriate amount | Appropriate amount | Appropriate amount | Appropriate amount |
| Perfume | Appropriate amount | Appropriate amount | Appropriate amount | Appropriate amount | Appropriate amount |
| Purified water | Balance | Balance | Balance | Balance | Balance |
| pH | 3.0 | 3.5 | 3.3 | 2.5 | 2.8 |
| Texture of hair after use (smoothness) | AA | AA | AA | BB | AA |
| Texture of hair during rinsing (smoothness) | AA | AA | AA | BB | AA |
| Stability (viscosity) | BB | BB | BB | BB | BB |
| Stability (turbidity, precipitation, separation) | BB | BB | BB | BB | BB |
| Degree of staining of the skin | BB | BB | BB | BB | BB |

TABLE 2

|  | Ex. 6 | Ex. 7 | Ex. 8 | Ex. 9 | Ex. 10 |
|---|---|---|---|---|---|
| Sodium N-stearoyl-N-methyl taurate | 5.0 | 10.0 | 1.0 | 1.0 | 0.1 |
| Sodium cocoyl isethionate | — | — | 1.0 | 1.0 | — |
| Sodium N-palmitoyl taurate | — | — | — | — | — |
| Sodium stearyl sulfate | — | — | — | — | 2.0 |
| Stearyl alcohol | 12.5 | 25.0 | 5.0 | 10.0 | 5.0 |
| Behenyl alcohol | — | — | — | — | — |
| Dimethylpolysiloxane (6 cs) | — | — | 2.0 | 2.0 | 2.0 |
| Emulsion-polymerized dimethylpolysiloxane(*) | 2.0 | 2.0 | 2.0 | 2.0 | 2.0 |
| Black No. 401 | 0.2 | 0.2 | 0.2 | 0.2 | 0.2 |
| Violet No. 401 | 0.3 | 0.3 | 0.3 | 0.3 | 0.3 |
| Yellow No. 4 | 0.3 | 0.3 | 0.3 | 0.3 | 0.3 |
| Benzyl alcohol | 4.0 | 4.0 | 4.0 | 4.0 | 4.0 |
| Citric acid | Appropriate amount | Appropriate amount | Appropriate amount | Appropriate amount | Appropriate amount |
| Preservative | Appropriate amount | Appropriate amount | Appropriate amount | Appropriate amount | Appropriate amount |
| Perfume | Appropriate amount | Appropriate amount | Appropriate amount | Appropriate amount | Appropriate amount |
| Purified water | Balance | Balance | Balance | Balance | Balance |
| pH | 4.0 | 4.5 | 3.0 | 3.1 | 3.3 |
| Texture of hair after use (smoothness) | AA | AA | BB | BB | BB |
| Texture of hair during rinsing (smoothness) | AA | BB | AA | AA | AA |
| Stability (viscosity) | BB | BB | BB | BB | BB |
| Stability (turbidity, precipitation, separation) | BB | BB | BB | BB | BB |

TABLE 2-continued

|  | Ex. 6 | Ex. 7 | Ex. 8 | Ex. 9 | Ex. 10 |
|---|---|---|---|---|---|
| Degree of staining of the skin | AA | AA | BB | BB | BB |

TABLE 3

|  | Comp. Ex. 1 | Comp. Ex. 2 | Comp. Ex. 3 | Comp. Ex. 4 | Comp. Ex. 5 | Comp. Ex. 6 |
|---|---|---|---|---|---|---|
| Sodium N-stearoyl-N-methyl taurate | — | 0.01 | 2.0 | 2.0 | — | — |
| Sodium cocoyl isethionate | — | — | — | — | 2.0 | — |
| Sodium N-palmitoyl taurate | — | — | — | — | — | 2.0 |
| Sodium stearyl sulfate | 2.0 | — | — | — | — | — |
| Stearyl alcohol | 5.0 | 2.5 | 50.0 | — | — | — |
| Behenyl alcohol | — | — | — | — | — | — |
| Dimethylpolysiloxane (6 cs) | 2.0 | 2.0 | 2.0 | 2.0 | 2.0 | 2.0 |
| Emulsion-polymerized dimethylpolysiloxane(*) | 2.0 | 2.0 | 2.0 | 2.0 | — | 2.0 |
| Black No. 401 | 0.2 | 0.2 | 0.2 | 0.2 | 0.2 | 0.2 |
| Violet No. 401 | 0.3 | 0.3 | 0.3 | 0.3 | 0.3 | 0.3 |
| Yellow No. 4 | 0.3 | 0.3 | 0.3 | 0.3 | 0.3 | 0.3 |
| Benzyl alcohol | 4.0 | 4.0 | 4.0 | 4.0 | 4.0 | 4.0 |
| Citric acid | Appropriate amount | Appropriate amount | Appropriate amount | Appropriate amount | Appropriate amount | Appropriate amount |
| Preservative | Appropriate amount | Appropriate amount | Appropriate amount | Appropriate amount | Appropriate amount | Appropriate amount |
| Perfume | Appropriate amount | Appropriate amount | Appropriate amount | Appropriate amount | Appropriate amount | Appropriate amount |
| Purified water | Balance | Balance | Balance | Balance | Balance | Balance |
| pH | 3.2 | 3.5 | 4.7 | 3.3 | 3.5 | 3.7 |
| Texture of hair after use (smoothness) | AA | DD | DD | CC | DD | DD |
| Texture of hair during rinsing (smoothness) | AA | DD | DD | DD | DD | CC |
| Stability (viscosity) | BB | DD | CC | DD | DD | DD |
| Stability (turbidity, precipitation, separation) | DD | DD | DD | DD | DD | DD |
| Degree of staining of the skin | CC | CC | AA | CC | CC | CC |

TABLE 4

|  | Ex. 11 | Comp. Ex. 7 | Comp. Ex. 8 | Comp. Ex. 9 | Comp. Ex. 10 |
|---|---|---|---|---|---|
| Sodium N-stearoyl-N-methyl taurate | 2.0 | — | — | — | — |
| Stearyltrimethyl-ammonium chloride | — | 2.0 | — | — | — |
| Keltrol | — | — | 1.0 | 1.0 | 1.0 |
| Bentonite | — | — | — | 0.5 | 0.5 |
| Carboxyvinyl polymer | — | — | — | — | 0.3 |
| Behenyl alcohol | 5.0 | 5.0 | — | — | — |
| Dimethylpolysiloxane (6 cs) | 2.0 | 2.0 | — | — | — |
| Emulsion-polymerized dimethylpolysiloxane(*) | 2.0 | 2.0 | — | — | — |
| Black No. 401 | 0.2 | 0.2 | 0.2 | 0.2 | 0.2 |
| Violet No. 401 | 0.3 | 0.3 | 0.3 | 0.3 | 0.3 |
| Yellow No. 4 | 0.3 | 0.3 | 0.3 | 0.3 | 0.3 |
| Benzyl alcohol | 4.0 | 4.0 | 4.0 | 4.0 | 4.0 |
| Citric acid | Appropriate amount | Appropriate amount | Appropriate amount | Appropriate amount | — |
| Potassium hydroxide | — | — | — | — | Appropriate amount |
| Preservative | Appropriate amount | Appropriate amount | Appropriate amount | Appropriate amount | Appropriate amount |

TABLE 4-continued

|  | Ex. 11 | Comp. Ex. 7 | Comp. Ex. 8 | Comp. Ex. 9 | Comp. Ex. 10 |
|---|---|---|---|---|---|
| Perfume | Appropriate amount | Appropriate amount | Appropriate amount | Appropriate amount | Appropriate amount |
| Purified water | Balance | Balance | Balance | Balance | Balance |
| pH | 2.0 | 3.0 | 3.0 | 3.2 | 2.7 |
| Texture of hair after use (smoothness) | AA | BB | DD | DD | DD |
| Texture of hair during rinsing (smoothness) | AA | AA | DD | DD | DD |
| Stability (viscosity) | BB | BB | DD | BB | BB |
| Stability (turbidity, precipitation, separation) | BB | DD | BB | BB | BB |
| Degree of staining of the skin | BB | CC | DD | DD | DD |

TABLE 5

|  | Ex. 12 | Ex. 13 | Ex. 14 | EX. 15 |
|---|---|---|---|---|
| Sodium N-stearoyl-N-methyl taurate | 2.0 | 2.0 | 2.0 | 2.0 |
| Cetanol | 5.0 | 5.0 | 5.0 | 5.0 |
| Behenyl alcohol | 5.0 | 5.0 | 5.0 | 5.0 |
| Dimethylpolysiloxane (6 cs) | 2.0 | 2.0 | 2.0 | 2.0 |
| Emulsion-polymerized dimethylpolysiloxane(*) | 2.0 | 2.0 | 2.0 | 2.0 |
| Orange No. 205 | 0.2 | 0.2 | 0.2 | 0.2 |
| Black No. 401 | 0.2 | 0.2 | 0.2 | 0.2 |
| Violet No. 401 | 0.1 | 0.1 | 0.1 | 0.1 |
| Carthamus yellow | 0.2 | 0.2 | 0.2 | 0.2 |
| Benzyl alcohol | 4.0 | 4.0 | 4.0 | 4.0 |
| Glycolic acid | 1.0 | — | — | — |
| Lactic acid | — | 1.0 | — | — |
| Phosphoric acid | — | — | 0.3 | — |
| Tartaric acid | — | — | — | 1.0 |
| Preservative | Appropriate amount | Appropriate amount | Appropriate amount | Appropriate amount |
| Perfume | Appropriate amount | Appropriate amount | Appropriate amount | Appropriate amount |
| Purified water | Balance | Balance | Balance | Balance |
| pH | 2.3 | 2.3 | 2.4 | 2.3 |
| Texture of hair after use (smoothness) | AA | AA | AA | AA |
| Texture of hair during rinsing (smoothness) | AA | AA | AA | AA |
| Stability (viscosity) | BB | BB | BB | BB |
| Stability (turbidity, precipitation, separation) | BB | BB | BB | BB |
| Degree of staining of the skin | BB | BB | BB | BB |

TABLE 6

|  | Ex. 16 |
|---|---|
| Sodium N-stearoyl-N-methyl taurate | 2.0 |
| Stearyl alcohol | 5.0 |
| Behenyl alcohol | 5.0 |
| Dimethylpolysiloxane (6 cs) | 2.0 |
| Emulsion-polymerized dimethylpolysiloxane(*) | 2.0 |
| Perilla color | 0.2 |
| Lithospermum root color | 0.2 |
| Red cabbage color | 0.1 |
| Carthamus yellow | 0.2 |
| Benzyl alcohol | 4.0 |
| Citric acid | 0.3 |
| Preservative | Appropriate amount |
| Perfume | Appropriate amount |
| Purified water | Balance |
| pH | 2.7 |
| Texture of hair after use (smoothness) | AA |
| Texture of hair during rinsing (smoothness) | AA |
| Stability (viscosity) | BB |
| Stability (turbidity, precipitation, separation) | BB |
| Degree of staining of the skin | BB |

As shown in Tables 1 through 6, when the hair dye composition of the present invention is stored for a long period of time, virtually no reduction or no reduction in viscosity is observed, although the composition has a pH in a strongly acidic region, in which the acid dye exerts its dyeing effects. In addition, the hair dye composition exhibits excellent long-term stability; i.e., turbidity, precipitation, and separation do not occur in the composition, and the composition provides excellent sensation upon use; i.e., the hair does not produce any tactile frictional resistance between fibers during rinsing, and unruliness of the hair does not occur after drying the hair. Furthermore, the degree of staining of the skin falls within an acceptable range during use of the hair dye composition, and the composition can be readily rinsed off after use thereof.

Example 17

| (Components) | (wt. %) |
|---|---|
| Black No. 401 | 0.2 |
| Violet No. 401 | 0.3 |
| Yellow No. 4 | 0.1 |
| Benzyl alcohol | 5.0 |
| Sodium N-lauroyl taurate | 2.0 |
| Stearyl alcohol | 5.0 |
| Xanthan gum | 1.5 |
| Cross-linked sodium polyacrylate | 0.2 |
| 1,3-Butylene glycol | 10.0 |
| Hydrolyzed collagen | 0.2 |
| Citric acid | 0.4 |
| Perfume | Appropriate amount |
| Ion-exchange water | Balance |

The hair dye composition having the above formulation, which had been produced by means of a customary method, exhibited excellent stability, high dyeability, excellent level dyeing property, and good color retention, and did not provide a sticky sensation upon use. In addition, the hair did not produce any tactile frictional resistance between fibers during rinsing and after the hair was dried Furthermore, the degree of staining of the hand with the composition fell within an acceptable range. The pH of the hair dye composition was found to be 2.5.

Example 18

| (Components) | (wt. %) |
|---|---|
| Black No. 401 | 0.2 |
| Violet No. 401 | 0.3 |
| Yellow No. 4 | 0.1 |
| 2-Phenoxyethanol | 5.0 |
| Octyl polyglycoside | 1.0 |
| Sodium N-lauroyl-N-methyl taurate | 2.5 |
| Cetostearyl alcohol | 10.0 |
| Bentonite | 1.7 |
| Dipropylene glycol | 12.0 |
| Citric acid | 1.0 |
| Hydrolyzed keratin | 0.1 |
| Perfume | Appropriate amount |
| Ion-exchange water | Balance |

The hair dye composition having the above formulation, which had been produced by means of a customary method, exhibited excellent stability, high dyeability, excellent level dyeing property, and good color retention, and did not provide a sticky sensation upon use. In addition, the hair did not produce any tactile frictional resistance between fibers during rinsing and after the hair was dried. Furthermore, the degree of staining of the hand with the composition fell within an acceptable range. The pH of the hair dye composition was found to be 2.2.

Example 19

| (Components) | (wt. %) |
|---|---|
| Black No. 401 | 0.2 |
| Violet No. 401 | 0.3 |
| Yellow No. 4 | 0.1 |
| Benzyl alcohol | 5.0 |
| Potassium cocoyl isethionate | 1.0 |
| Cetyl alcohol | 3.0 |
| Tamarind gum | 2.5 |
| Bentonite | 3.2 |
| Dimethylpolysiloxane | 0.5 |
| N-Methylpyrrolidone | 10.0 |
| Citric acid | 4.0 |
| Glycerin | 0.5 |
| Polyoxyethylene (100) hydrogenated castor oil ester | 1.0 |
| Hydrolyzed silk protein | 0.1 |
| Perfume | Appropriate amount |
| Ion-exchange water | Balance |

The hair dye composition having the above formulation, which had been produced by means of a customary method, exhibited excellent stability, high dyeability, excellent level dyeing property, and good color retention, and did not provide a sticky sensation upon use. In addition, the hair did not produce any tactile frictional resistance between fibers during rinsing and after the hair was dried. Furthermore, the degree of staining of the hand with the composition fell within an acceptable range. The pH of the hair dye composition was found to be 2.1.

Example 20

| (Components) | (wt. %) |
|---|---|
| Black No. 401 | 0.2 |
| Violet No. 401 | 0.3 |
| Yellow No. 4 | 0.1 |
| Benzyl alcohol | 5.0 |
| Sodium cocoyl isethionate | 1.0 |
| Behenyl alcohol | 6.0 |
| Dimethylpolysiloxane | 0.5 |
| N-Methylpyrrolidone | 13.5 |
| Phosphoric acid | 2.0 |
| Glycerin | 0.5 |
| Hydrolyzed elastin | 0.2 |
| Polyoxyethylene (100) hydrogenated castor oil ester | 1.0 |
| Perfume | Appropriate amount |
| Ion-exchange water | Balance |

The hair dye composition having the above formulation, which had been produced by means of a customary method, exhibited excellent stability, high dyeability, excellent level dyeing property, and good color retention, and did not provide a sticky sensation upon use. In addition, the hair did not produce any tactile frictional resistance between fibers during rinsing and after the hair was dried. Furthermore, the degree of staining of the hand with the composition fell

Example 21

| (Components) | (wt. %) |
| --- | --- |
| Black No. 401 | 0.2 |
| Violet No. 401 | 0.3 |
| Yellow No. 4 | 0.1 |
| Benzyl alcohol | 8.0 |
| Sodium N-myristoyl taurate | 5.0 |
| Behenyl alcohol | 15.0 |
| Polyether-modified polysiloxane | 0.5 |
| Dimethylpolysiloxane | 0.5 |
| Tetrahydrofurfuryl alcohol | 12.0 |
| Citric acid | 3.0 |
| Glycerin | 0.5 |
| Carboxymethyl cellulose | 0.1 |
| Polyoxyethylene (100) hydrogenated castor oil ester | 1.0 |
| Hydrolyzed keratin | 0.2 |
| Perfume | Appropriate amount |
| Ion-exchange water | Balance |

The hair dye composition having the above formulation, which had been produced by means of a customary method, exhibited excellent stability, high dyeability, excellent level dyeing property, and good color retention, and did not provide a sticky sensation upon use. In addition, the hair did not produce any tactile frictional resistance between fibers during rinsing and after the hair was dried. Furthermore, the degree of staining of the hand with the composition fell within an acceptable range. The pH of the hair dye composition was found to be 2.5.

Example 22

| (Components) | (wt. %) |
| --- | --- |
| Black No. 401 | 0.02 |
| Violet No. 401 | 0.03 |
| Yellow No. 4 | 0.01 |
| Benzyl alcohol | 3.0 |
| Sodium stearoyl isethionate | 4.0 |
| Stearyl alcohol | 10.0 |
| Citric acid | 0.6 |
| Glycerin | 0.5 |
| Polyoxyethylene (100) hydrogenated castor oil ester | 0.7 |
| 1.3-Butylene glycol | 15.0 |
| Quaternarized hydrolyzed collagen | 0.2 |
| Perfume | Appropriate amount |
| Ion-exchange water | Balance |

The hair dye composition having the above formulation, which had been produced by means of a customary method, exhibited excellent stability, high dyeability, excellent level dyeing property, and good color retention, and did not provide a sticky sensation upon use. In addition, the hair did not produce any tactile frictional resistance between fibers during rinsing and after the hair was dried. Furthermore, the degree of staining of the hand with the composition fell within an acceptable range. The pH of the hair dye composition was found to be 4.0.

Example 23

| (Components) | (wt. %) |
| --- | --- |
| Black No. 401 | 0.02 |
| Violet No. 401 | 0.03 |
| Yellow No. 4 | 0.01 |
| Benzyl alcohol | 3.0 |
| Sodium N-stearoyl-N-methyl taurate | 3.0 |
| Stearyl alcohol | 8.0 |
| Polyether-modified polysiloxane | 0.2 |
| Dimethylpolysiloxane | 0.5 |
| Tetrahydrofurfuryl alcohol | 8.7 |
| Citric acid | 0.6 |
| Glycerin | 0.5 |
| Octamethylcyclotetrasiloxane | 3.0 |
| Polyoxyethylene (100) hydrogenated castor oil ester | 0.7 |
| 1,3-Butylene glycol | 15.0 |
| Xanthan gum | 0.5 |
| Bentonite | 0.3 |
| Quaternarized hydrolyzed silk protein | 0.2 |
| Perfume | Appropriate amount |
| Ion-exchange water | Balance |

The hair dye composition having the above formulation, which had been produced by means of a customary method, exhibited excellent stability, high dyeability, excellent level dyeing property, and good color retention, and did not provide a sticky sensation upon use. In addition, the hair did not produce any tactile frictional resistance between fibers during rinsing and after the hair was dried. Furthermore, the degree of staining of the hand with the composition fell within an acceptable range. The pH of the hair dye composition was found to be 3.8.

Example 24

| (Components) | (wt. %) |
| --- | --- |
| Black No. 401 | 0.02 |
| Violet No. 401 | 0.03 |
| Yellow No. 4 | 0.01 |
| Benzyl alcohol | 5.0 |
| Sodium N-stearoyl-N-methyl taurate | 4.8 |
| Cetyl alcohol | 10.0 |
| Behenyl alcohol | 4.6 |
| Dimethylpolysiloxane | 4.5 |
| Cetyl octanoate | 3.0 |
| Citric acid | 0.42 |
| Isopropylene glycol | 5.0 |
| Methylparaben | 0.1 |
| Perfume | Appropriate amount |
| Ion-exchange water | Balance |

The hair dye composition having the above formulation, which had been produced by means of a customary method, exhibited excellent stability, high dyeability, excellent level dyeing property, and good color retention, and did not provide a sticky sensation upon use. In addition, the hair did not produce any tactile frictional resistance between fibers during rinsing and after the hair was dried. Furthermore, the degree of staining of the hand with the composition fell within an acceptable range. The pH of the hair dye composition was found to be 4.2.

INDUSTRIAL APPLICABILITY

As described above in detail, the present invention provides a hair dye composition which is stable even in a strongly acidic region (pH of 1.5 to 4.5) in which an acid dye exerts its dyeing effects, which has appropriate viscosity, which provides excellent sensation upon use, and which can be easily rinsed off after use thereof.

The invention claimed is:

1. A hair dye composition comprising a component (A), which is a long-chain acyl sulfonic acid salt anionic surfactant represented by the following formula (I):

$$R_1CO\text{-a-}(CH_2)_n SO_3 M_1 \qquad (I),$$

wherein $R_1CO$— represents a saturated or unsaturated fatty acid residue (acyl group) having an average carbon atom number of 10 to 22; a represents —O— or —NR—, wherein R represents a hydrogen atom or a C1–C3 alkyl group; $M_1$ represents a hydrogen atom, an alkali metal, an alkaline earth metal, an ammonium, or an organic amine; and n represents an integer of 1 to 3, in an amount of 0.1 to 10.0 wt. %; a component (B), which is an aliphatic alcohol, in an amount of 0.25 to 25.0 wt. %; a component (C), which is an acid dye and/or a natural dyestuff, and a component (D), which is an emulsion of non-volatile silicone.

2. The hair dye composition as recited in claim 1, further comprising benzyl alcohol and wherein the ratio by weight of the component (A) to the component (B) is 1:2.5 to 1:50.

3. The hair dye composition as recited in claim 1, wherein the component (C) is contained in an amount of 0.001 to 2.0 wt. %.

4. The hair dye composition as recited in claim 1, wherein the pH of the composition is 1.5 to 4.5.

* * * * *